United States Patent [19]

Sandock

[11] Patent Number: 5,800,519
[45] Date of Patent: Sep. 1, 1998

[54] TUBULAR MEDICAL PROSTHESIS FOR USE IN A BODY LUMEN

[75] Inventor: David L. Sandock, Littleton, Mass.

[73] Assignee: Kopin Corporation, Taunton, Mass.

[21] Appl. No.: 743,395

[22] Filed: Nov. 4, 1996

Related U.S. Application Data

[63] Continuation of Ser. No. 236,786, Apr. 29, 1994, abandoned.

[51] Int. Cl.⁶ .................................. A61F 2/04; A61F 2/06
[52] U.S. Cl. ........................ 623/1; 606/194; 623/12
[58] Field of Search ........................ 623/1, 12; 606/192, 606/194, 195, 198, 108

[56] References Cited

U.S. PATENT DOCUMENTS

| | | |
|---|---|---|
| 3,425,418 | 2/1969 | Chvapil et al. . |
| 3,868,956 | 3/1975 | Alfidi et al. ............... 606/194 |
| 4,776,337 | 10/1988 | Palmaz . |
| 4,856,516 | 8/1989 | Hillstead . |
| 4,922,905 | 5/1990 | Strecker . |
| 4,950,227 | 8/1990 | Savin et al. ............... 606/192 |
| 4,969,458 | 11/1990 | Wiktor ............... 606/194 |
| 4,994,071 | 2/1991 | MacGregor ............... 606/194 |
| 5,019,090 | 5/1991 | Pinchuk ............... 606/194 |
| 5,035,706 | 7/1991 | Giantureo et al. . |
| 5,041,126 | 8/1991 | Gianturco ............... 606/195 |
| 5,061,275 | 10/1991 | Wallsten et al. . |
| 5,084,065 | 1/1992 | Weldon et al. ............... 623/12 |
| 5,116,365 | 5/1992 | Hillstead . |
| 5,171,262 | 12/1992 | MacGregor . |
| 5,226,913 | 7/1993 | Pinchuk ............... 623/1 |
| 5,234,457 | 8/1993 | Andersen ............... 606/195 |
| 5,282,823 | 2/1994 | Schwartz et al. ............... 606/198 |
| 5,290,305 | 3/1994 | Inoue ............... 606/194 |
| 5,314,472 | 5/1994 | Fontaine ............... 623/12 |
| 5,342,348 | 8/1994 | Kaplan ............... 606/198 |
| 5,354,309 | 10/1994 | Schnepp-Pesch et al. ............... 606/198 |
| 5,360,443 | 11/1994 | Barone et al. ............... 606/194 |
| 5,382,259 | 1/1995 | Phelps et al. ............... 606/151 |
| 5,527,354 | 6/1996 | Fontaine et al. ............... 623/1 |
| 5,643,339 | 7/1997 | Kavteladze et al. ............... 623/1 |

FOREIGN PATENT DOCUMENTS

| | | |
|---|---|---|
| 0 565 251 A1 | 3/1993 | European Pat. Off. . |
| 0 556 850 A1 | 8/1993 | European Pat. Off. . |
| 94 17754 | 2/1993 | WIPO ............... 623/1 |
| WO 94/00178 | 1/1994 | WIPO . |
| WO 94/03127 | 2/1994 | WIPO . |

*Primary Examiner*—Mickey Yu
*Assistant Examiner*—Bruce E. Snow
*Attorney, Agent, or Firm*—Hamilton, Brook, Smith & Reynolds, PC

[57] ABSTRACT

An implantable self-expanding medical prosthesis. The prosthesis has a tube-form body with a body wall structure having a geometric pattern of cells defined by a series of elongate strands extending to regions of intersection and interlocking joints at said regions of intersection formed by a portion of at least one of said strands being helically wrapped about a portion of another.

41 Claims, 8 Drawing Sheets

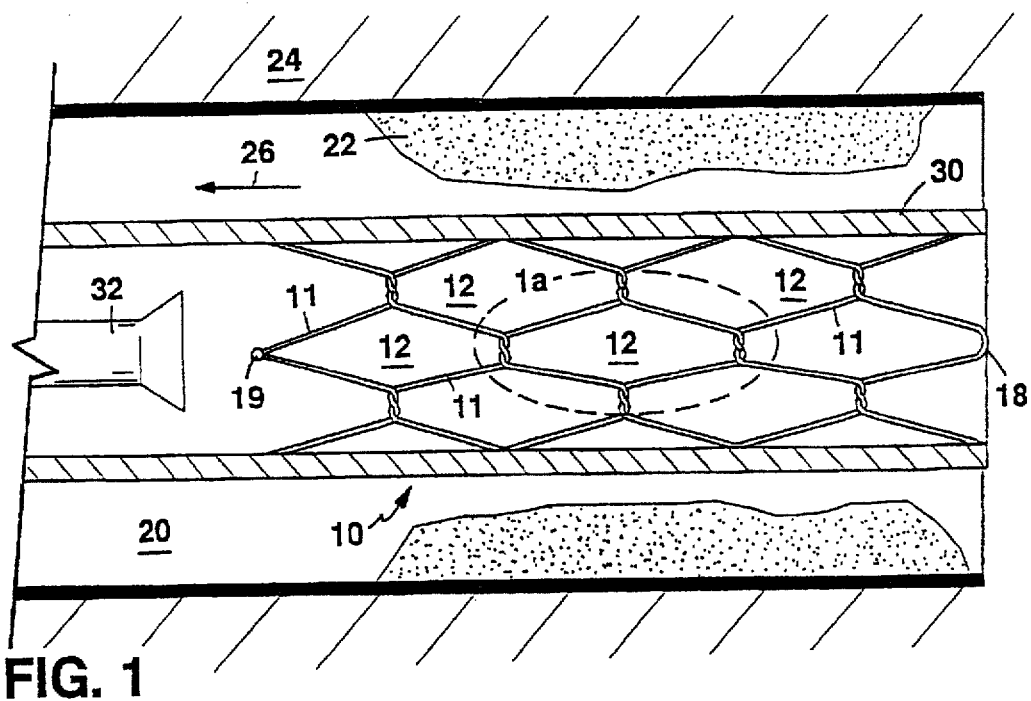
FIG. 1
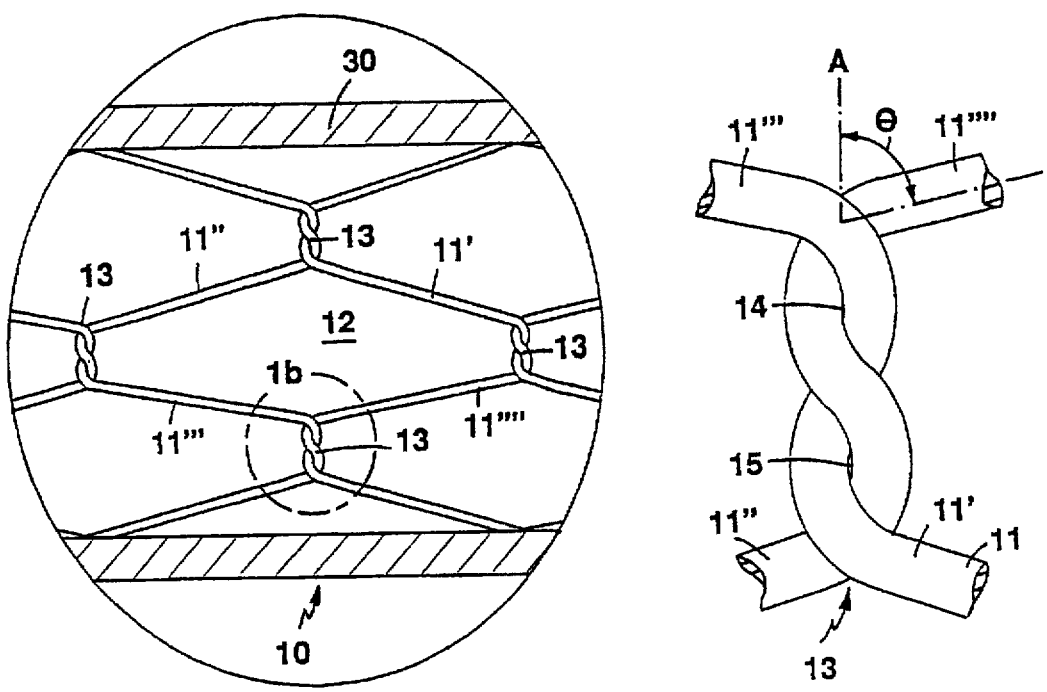
FIG. 1a
FIG. 1b

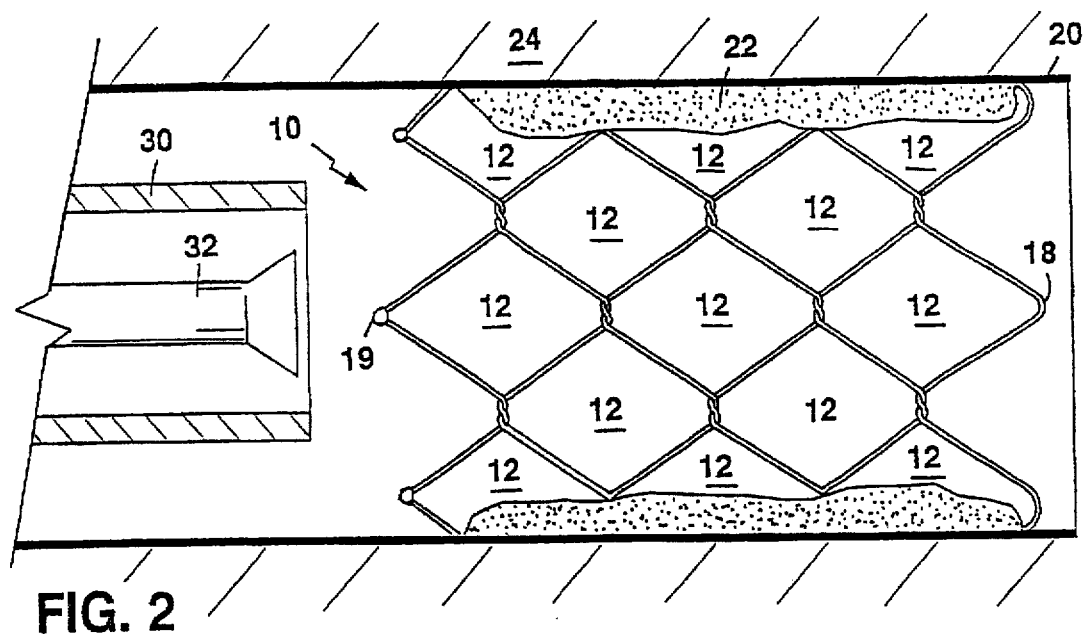
FIG. 2
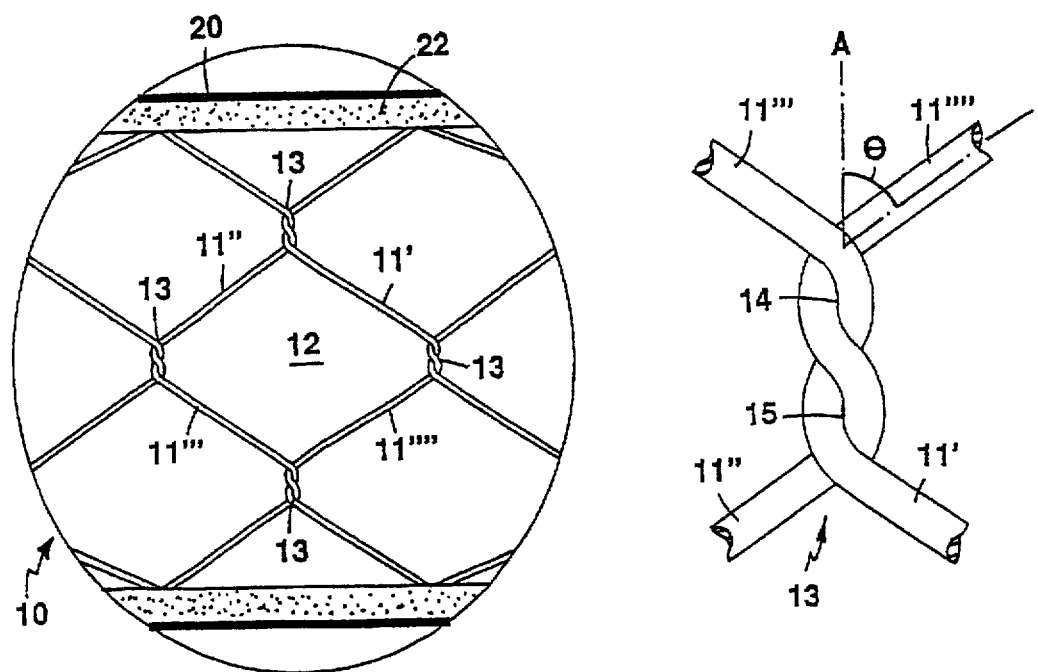
FIG. 2a
FIG. 2b

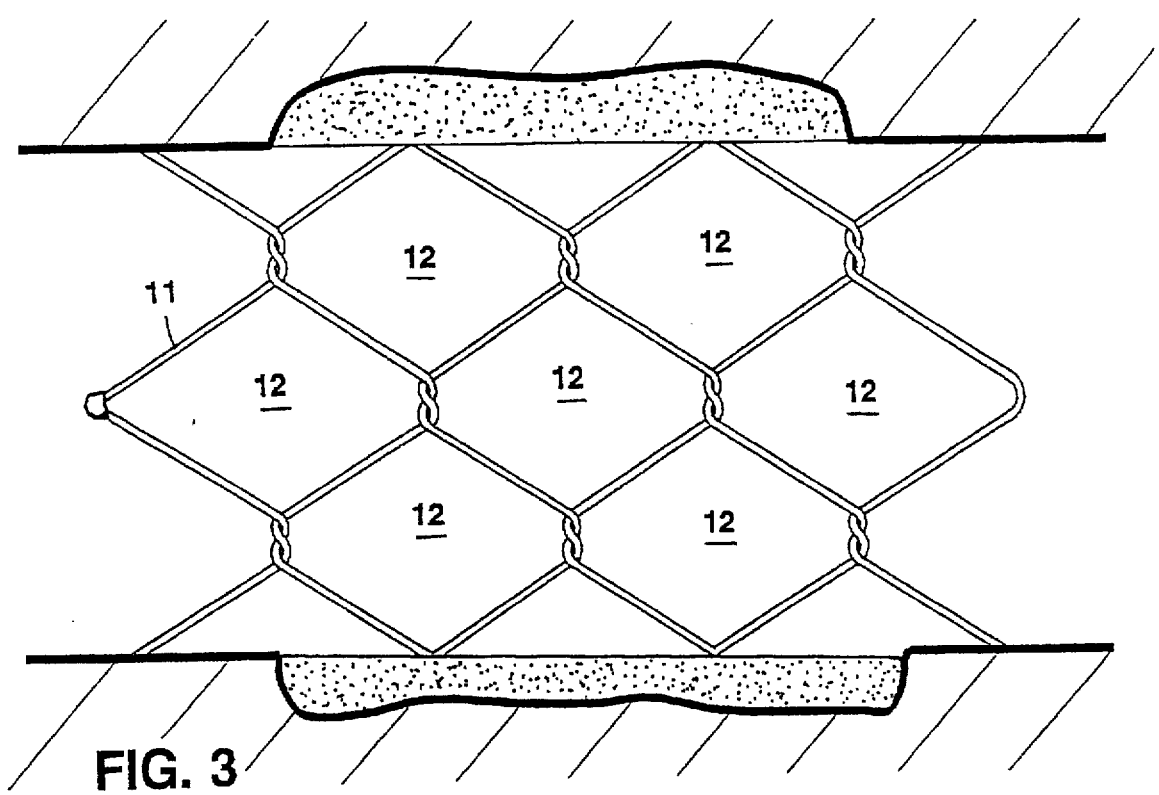
FIG. 3
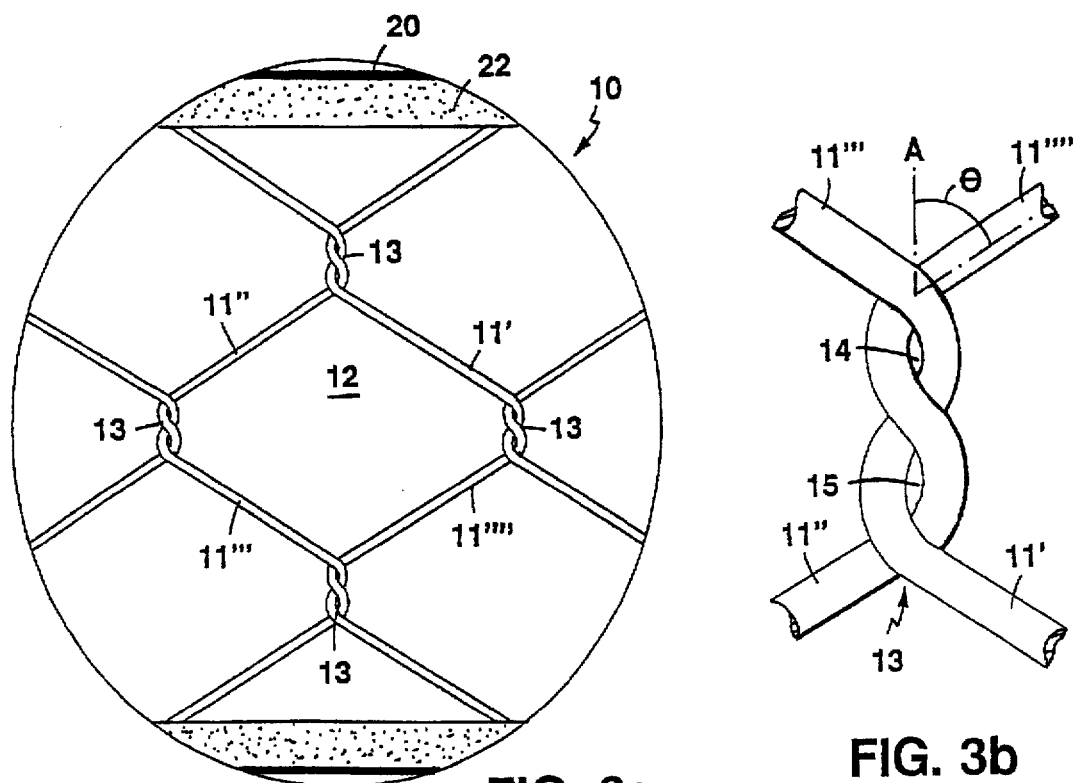
FIG. 3a
FIG. 3b

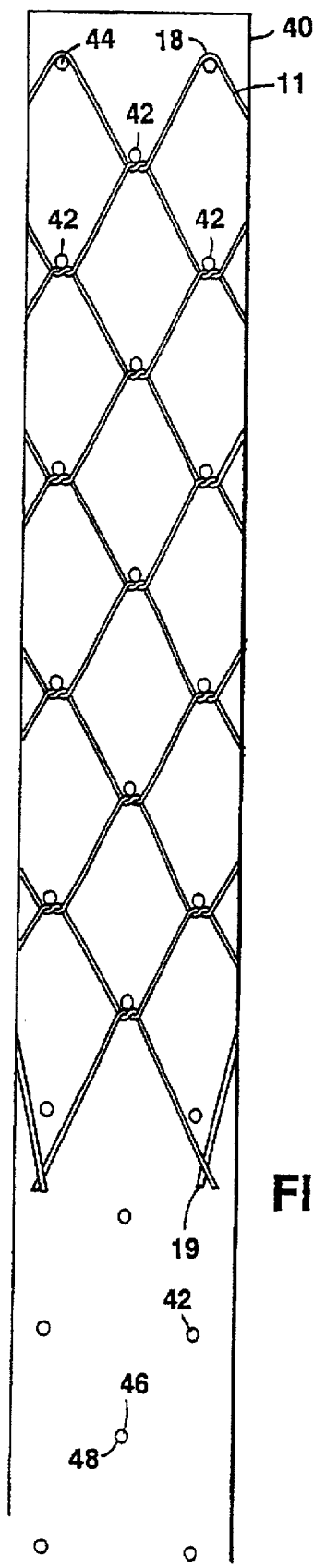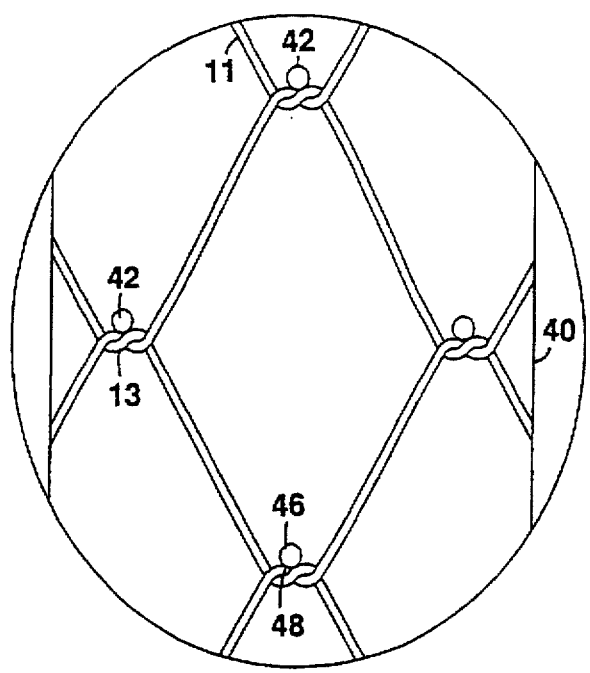
FIG. 5a
FIG. 5

TUBULAR MEDICAL PROSTHESIS FOR USE IN A BODY LUMEN

This is a continuation of application Ser. No. 08/236,786, filed Apr. 29, 1994, now abandoned.

FIELD OF THE INVENTION

This invention relates to tubular medical prostheses to be used inside the body.

BACKGROUND OF THE INVENTION

Medical prostheses, such as stents, are placed within the body to treat a body lumen that has been occluded, for example, by a tumor. The medical prostheses may be formed of wire configured into a tube and are usually delivered into the body lumen using a catheter. The catheter carries the prosthesis in a reduced-size form to the desired site. When the desired location is reached, the prothesis is released from the catheter and expanded so that it engages the lumen wall.

A self-expanding prosthesis is made of highly elastic materials. It is held in a compressed condition during delivery to this site by, for example, a sheath. Upon reaching the desired site, the sheath constraining the prosthesis is pulled proximally, while the prosthesis is held in the desired position, enabling the prosthesis to self-expand by its own elastic restoring force.

A non-self-expanding prosthesis is made of less elastic, plastically deformable materials. It is positioned over a mechanical expander, such as a balloon, which can be inflated to force the prosthesis radially outward once the desired site is reached.

SUMMARY OF THE INVENTION

In a first aspect, the invention features an implantable medical prosthesis. The prosthesis is a tube-form body with a body wall structure having a geometric pattern of cells defined by a series of elongate strands extending to regions of intersection. The prosthesis has interlocking joints at the regions of intersection formed by a portion of at least one of the strands being helically wrapped about a portion of another strand.

Embodiments may include one or more of the following. Portions of the strands are helically wrapped about each other. The interlocking joints are constructed such that the axis of the helically wrapped portion is oriented generally circumferentially with respect to the tube-form body. The interlocking joints are also constructed such that the helically wrapped portions of the strands can move relative to each other when the prosthesis is subject to varying radial compressive forces while still maintaining the cell structure. The strands are helically wrapped through a single 360 degree rotation and are metal wires composed of a Nickel-Titanium alloy. The prosthesis is self-expanding. The prosthesis includes a sleeve-type covering. The prosthesis is constructed for use in the biliary system and has a fully expanded diameter of about 10 mm, and is compressible to a diameter of about 9 French without plastic deformation. The prosthesis is constructed to plastically deform during expansion. The prosthesis is also constructed of a shape memory material to enable expansion in response to a temperature change. The prosthesis includes a drug-delivery layer carried by the wall structure. The prosthesis is constructed as a temporary stent, such that an end of the stent is connected to a drawing member that permits withdrawing the stent after deployment.

In another aspect, the invention features a method for creating a tubular medical prosthesis by providing a mandrel of size selected to substantially correspond to the diameter of the stent, the mandrel being adapted to removably receive a pattern of radially extending pegs, by providing elastic wire strands, and forming the prosthesis by fixing the strands at one end corresponding to an end of the prosthesis, drawing the adjacent strands to an adjacent, axially spaced peg, joining the strands such that the peg maintains the drawn portions of the strands in tension, repeating the drawing and joining to form a tubular member of desired length, and removing the prosthesis from the mandrel by expansion.

In embodiments, the method may also include one or more of the following. The method may include providing a mandrel formed of a heat-resistant material, and heat-treating the mandrel and the prosthesis prior to removing the prosthesis from the mandrel. The method may include fixing the ends of the strands corresponding to the other end of the prosthesis, after heat-treating said prosthesis. The method may include joining the strands by helically wrapping the strands about each other. The method may include providing a mandrel adapted to receive the pegs in a diagonal pattern extending axially along the length of the mandrel. The method may also include providing metal wire strands formed of a nickel-titanium alloy.

In another aspect, the invention features a system for treating an occluded body lumen. The system includes a prosthesis having a tube-form body with a body wall structure having a geometric pattern of cells defined by a series of elongate strands extending to regions of intersection, and interlocking joints at the regions of intersection formed by portions of the strands that are helically wrapped about each other. The system also includes a delivery catheter constructed to receive the prosthesis in a compact state for delivery through the body to a desired site in the body lumen, and to allow expansion of the prosthesis to larger diameters for engaging the body lumen at the desired site. The delivery catheter includes a sheath constructed to maintain the prosthesis in compact form during the delivery. The interlocking joints of the prosthesis are constructed such that the axes of the helices of the helically wrapped portions of the strands are oriented generally circumferentially with respect to the tube-form body. The interlocking joints are also constructed such that the helically wrapped portions of the strands can move relative to each other when the prosthesis is subject to varying radial compressive force while still maintaining said cell structure. The strands forming the interlocking joints are helically wrapped through a single 360 degree rotation and are metal wires composed of an Nickel-Titanium alloy. The system may be constructed for use in the biliary system such that the prosthesis has a fully expanded diameter of about 10 mm, and be compressible to a diameter of about 9 French, without plastic deformation.

In another aspect, the invention features a method for treating a body lumen. The method may include using a prosthesis having a tube-form body with a body wall structure having a geometric pattern of cells defined by a series of elongate strands extending to regions of intersection, and interlocking joints at the regions of intersection formed by portions of the strands that are helically wrapped about each other, using a delivery catheter constructed to receive the prosthesis in a compact state for delivery through the body to a desired site in the body lumen and to allow expansion of the prosthesis to larger diameters for engaging the body lumen at the desired site, delivering the prosthesis to the site on the catheter, and releasing the prosthesis at the site.

In embodiments, the method may also include treating a body lumen having a highly torturous bend, by providing and delivering the prosthesis to the bend. The bend may approach 80°–90°.

Prostheses of the invention, such as stents, have an advantageous combination of properties. The stents can exert large radial outward forces that can open or maintain a lumen that has been occluded by disease. Yet the stents can also be compacted to a relatively small diameter so that they can be delivered into narrow lumens. The stent cell structure uniformly collapses in a preferential orientation permitting the stent to be compressed into a relatively small diameter. These properties are enabled by the stent construction. The cell structure of the stent wall contributes to the large radial forces since adjacent cells reinforce each other and allow force transmission along the length of the stent. Interlocking joints, preferably arranged with joint axes extended in circumferential fashion, maintain the cell structure at all levels of expansion and compression. The joints allow an elastic pivoting of the wires at the joint. The joints also distribute stresses along the lengths of the wire portions forming the joints and adjust slightly by loosening and tightening. The joints are highly resistant to failure by shear forces, even when repeatedly compressed and expanded. The stents are effective in highly tortuous passageways since they resist buckling when bent to extreme radii, thus maintaining an open path through the stent. Yet, the stent is relatively flexible such that it bends easily as it is being delivered in a catheter into the tortuous passageway. The stents also exhibit only a small difference in axial length between compressed and expanded states. Moreover, the prostheses can be manufactured readily and in a cost-effective manner.

Other features and advantages follow.

BRIEF DESCRIPTION OF THE DRAWINGS

FIG. 1 is a cross-sectional side view of a medical prosthesis according to the invention compressed in a sheath during delivery into the body, while FIG. 1a is an enlarged view of the portion of the prosthesis in the region defined by line aa in FIG. 1 and FIG. 1b is a further enlarged view of the portion defined by the line bb in FIG. 1a;

FIG. 2 is a cross-sectional side view of the prosthesis immediately after placement at a desired site, in an intermediate state of expansion, while FIGS. 2a and 2b are enlarged views of portions of the prosthesis similar to FIGS. 1a and 1b;

FIG. 3 is a cross-sectional side view of the medical prosthesis after full expansion at the desired site, while FIGS. 3a and 3b are enlarged views of portions of the prosthesis similar to FIGS. 1a and 1b;

FIG. 4 is cross-sectional side view of a prosthesis in a bent configuration, while FIG. 4a is an end-on cross-sectional view of the prosthesis taken along lines a—a in FIG. 4 and FIG. 4b is an end-on cross-sectional view of the prosthesis taken along lines b—b in FIG. 4;

FIGS. 5–5a illustrate the manufacture of a prosthesis on a mandrel with FIG. 5 being a side view and FIG. 5a being an enlarged view of a portion of the prosthesis on the mandrel;

FIG. 6 is a cross-sectional side view of another prosthesis in an expanded state, while

FIG. 7 is a cross-sectional side view of another medical prosthesis, while

DESCRIPTION OF THE PREFERRED EMBODIMENTS

Figures 4, 4A, 4B:
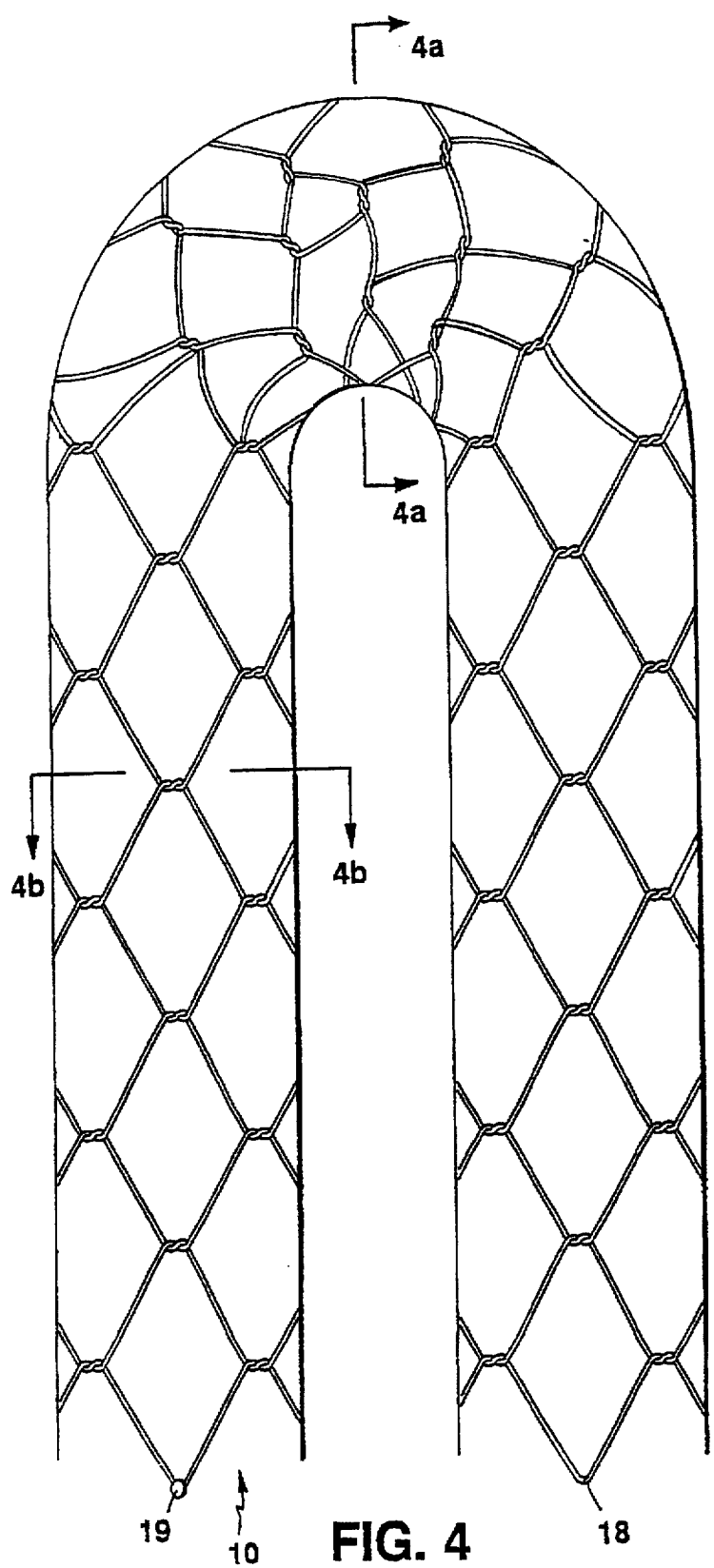

Referring to FIGS. 1–3c, a self-expanding medical prosthesis 10 according to the invention is shown in different stages of expansion. Referring to FIGS. 1 et seq., the prosthesis is introduced into a body lumen 20, such as a biliary tract, to the site of deployment inside a sleeve 30 that maintains the prosthesis in a compressed, reduced size. (The catheter may be delivered through the working channel of an endoscope, which, in this application, typically has a lumen diameter of about 10 french.) Referring to FIGS. 2 et seq., when the catheter is positioned within the body lumen at the site corresponding to an obstruction, such as, for example, occlusion 22, the sleeve 30 is withdrawn (arrow 26), enabling the medical prosthesis 10 to radially expand by its internal restoring forces and engage the occlusion and adjacent healthy wall of the lumen. (A member 32 is used to maintain the axial position of the medical prosthesis 10 as the catheter 30 is removed from about the medical prosthesis 10.) Referring to FIGS. 3 et seq., in a short time after the deployment, the prosthesis expands and pushes the lumen walls outward to fully open the lumen.

Referring to these figures, particularly the enlarged views, the prosthesis is formed of elongate strands 11, such as elastic metal wires, that are arranged to form a pattern of geometric cells 12. The sides of the cells are defined by strand lengths 11', 11", 11''', 11'''' that meet at regions of intersection. At the regions of intersection, the strands are helically wrapped about each other to form interlocking joints 13. The interlocking joints 13 are arranged so that the axes of the helices extend in the circumferential direction and are substantially in the plane of the stent wall. The strands extend at a strand angle θ which is defined between the axis, A, of the helical joint and the linear cell side-forming portion 11" of the strands.

Referring particularly to FIGS. 1 et seq., when the medical prosthesis 10 is radially compressed, the interlocking joints 13 are in tight interference such that the points 14 and 15 on the strands are in close contact. The portion of the elongate strands 11 forming the walls of the cells 12 are rotationally bent or deflected with respect to the joints, but remain substantially straight. The individual cells are generally rectangular. Strand angle θ is relatively large when compared to the size of this angle when the prosthesis is at full expansion, as will be discussed further below.

Referring to FIGS. 2 et seq., immediately after the prosthesis has been deployed into a body and has not yet pushed the occlusion 22 radially outward to fully open the lumen, the medical prosthesis 10 is in an intermediate compressed state. (Note that the distal 18 and proximal 19 ends of the medical prosthesis 10 are fully extended by the internal restoring forces of the prosthesis since the occlusion 22 is not present to interfere with the expansion of the medical prosthesis at these points.) Referring particularly to the enlarged views in FIGS. 2a and 2b, in this condition, the interlocking joints 13 loosen such that points 14 and 15 are slightly separated. The portions of the strands 11 forming the walls of the cells 12 rotate and the individual cells 12 approach a more diamond shape and shorten slightly. Strand angle θ decreases as the elongated strands 11 move relative to one another.

Referring to FIG. 3, at full expansion, the internal restoring force of the medical prosthesis pushes the occlusion 22 radially outward thus opening a passage way that allows unobstructed flow through the body lumen.

Referring to the enlarged views in FIGS. 3a and 3b, the interlocking joints 13 loosen further, the cells 12 are more diamond in shape and strand angle θ decreases further. The medical prosthesis 10 continues to apply a radially outward force sufficient to keep the lumen dilated.

Referring to FIGS. 4–4b, another property of the prosthesis 10 is that it can maintain a substantially open lumen in a body region of extreme curvature. Even with the prosthesis bent 90 degrees, its circumference deforms only slightly and is ovular in shape (FIG. 4a), while the circumference of the other portions of the medical prosthesis 10 remain circular (FIG. 4b). In the portion of the prosthesis along the outside of the curve, the prosthesis must adjust to large axial tension forces, while the portion of the prosthesis on the inside of the curve must adjust to large axial compression forces.

Referring now to FIGS. 5 and 5a, a method for making the medical prosthesis is illustrated. A forming mandrel 40 is chosen based on the desired diameter of the prosthesis. The mandrel 40 includes anchoring pins 44, 42 (extending radially about 1 mm) on its outer surface of the mandrel in a pattern that determines the geometric cell pattern. Strands 11 are bent around the top portion 46 of each top anchoring pin 44 to form the distal end 18 of the prosthesis. The strands 11 are then pulled diagonally downward to an adjacent anchoring pin 42 where they are joined. The strands 11 are helically wrapped about each other to form the interlocking joint 13, with each strand passing through a single 360 degree rotation. The two strands 11 are pulled taught so that the interlocking joint 13 rests firmly against the bottom portion 48 of anchoring pin 42 such that each strand is maintained in tension. The free ends of the strands are then pulled downward to the next diagonally adjacent anchoring pin 42. This process is continued until the desired length of the medical prosthesis is achieved.

The prosthesis is then heat-treated by placing the forming mandrel 40 with the medical prosthesis into a heating chamber (not shown). Prior to heat-treating, the wires, i.e., nitinol, are relatively malable. After heat treatment, the strands 11 at the proximal end 19 of the medical prosthesis are then joined, for example, by ball welding the ends of the wires. The wires at the end may also be are twisted helically (not shown), with the axis of the helices parallel to the stent axis, and then ball welding the ends. Alternatively, the wires at the proximal end of the prosthesis may be elastically bent around the bottom portion of each bottom anchoring pin and then slipped into a sleeve such as a spring (not shown), formed from, for example, of nitinol. The wires are then welded at at least one end of the spring so that they will not slip free. The prosthesis is then removed from the mandrel by axially compressing the prosthesis, which increases the radial diameter of the prosthesis, so that it can be pulled off of the forming mandrel. In an alternative embodiment, the strands 11 at the proximal end 19 of the medical prosthesis 10 may be joined prior to treatment in the chamber. In another embodiment, the pins are friction fit in holes in the mandrel and can be removed so that the prosthesis can be slipped off the mandrel.

The prosthesis may be constructed as a stent for use in a biliary tract. This application presents particular challenges in that the prosthesis must be collapsible to small size, about 9 French, for delivery into an occluded portion of the tract and must also be capable of relatively large radial expansion forces. Still, the expansion forces must not be so great that the compressed prosthesis damages the soft walls of the delivery sheath, which are preferably made of a polymer such as Teflon. The stent can damage the sheath by deforming it, which makes the sheath difficult to withdraw to release the stent at the point of the obstruction. In a preferred embodiment, the prosthesis has a maximum expanded diameter of about 10 mm. The length of the prosthesis is from about 6 cm to about 8 cm in the fully expanded condition. A prosthesis with a 10 mm fully expanded diameter exerts a radial force of about 0.6 lbs. at 5 mm diameter. (The radial force can be measured by placing the prosthesis in a tubular cell formed of two separable pieces and measuring the force on these pieces with an Instron force gauge.) The deployment force for a prosthesis of this size is about 1.0 lbs. (The deployment force can be measured by connecting the prosthesis to an Instron force gauge, placing the prosthesis into a teflon sheath (about 8.1 French, inner diameter), and while holding the sheath stationary, pulling the prosthesis through the sheath through a distance of at least one inch.) The prosthesis can be compressed to about 9 French and will not deform a teflon sheath with a 0.004 inch wall thickness. The length of the prosthesis increases only slightly when in the compressed state, e.g. about 20% or less. The prosthesis is formed of strands made from a highly elastic material, such as a nitinol, a nickel-titanium alloy. The number of strands used to form the prosthesis is 5 or 6. The diameter of the strands is between about 0.004 inch to about 0.008 inch, for example, 0.006 inch. The number of cells about the circumference of the prosthesis is five. The strand angle θ, when the stent is fully expanded, is 35°–55°, preferably 45°. The axial length and width of each cell is about 0.24 inch, when the stent is fully expanded. The forming mandrel is made of stainless steel. The prosthesis is heat-treated at about 450° C. for 20 minutes. The device can be delivered into the body using a sheath system as described above. Another system is described in U.S. Ser. No. 08/065,238, filed May 20, 1993, the entire contents being incorporated herein by reference. The sheath can be made of teflon or other materials (i.e., metals). (The strands are formed as discussed in U.S. Ser. No. 08/135,226, filed Oct. 13, 1993, the entire contents of which are incorporated herein by reference.)

The construction of the prosthesis can be varied for a particular application by varying, for example, the diameter, length, and cell structure (including the number, size, and geometry of the cells). The radial force that the prosthesis exerts can be increased for a prosthesis of a given fully expanded diameter by using smaller cells, i.e. a larger number of cells around the circumference, by decreasing the angle θ, by shortening the axial length of the cells relative to their width, and by increasing the diameter of the strands. The number and nature of helical rotations of the joints can be increased, e.g. so that one strand passes through one rotation and the other through two rotations or so that both strands pass through two or more rotations. This has the effect of lengthening the joints, which provides additional interlocking that helps the stent maintain the cellular structure in response to compressive forces and also reduces the radial force for a given diameter. The joints may be arranged so that one of the strand portions is helically wrapped around the other strand portion, which remains linear and on the axis of the helix of the other strand.

Figure 6:
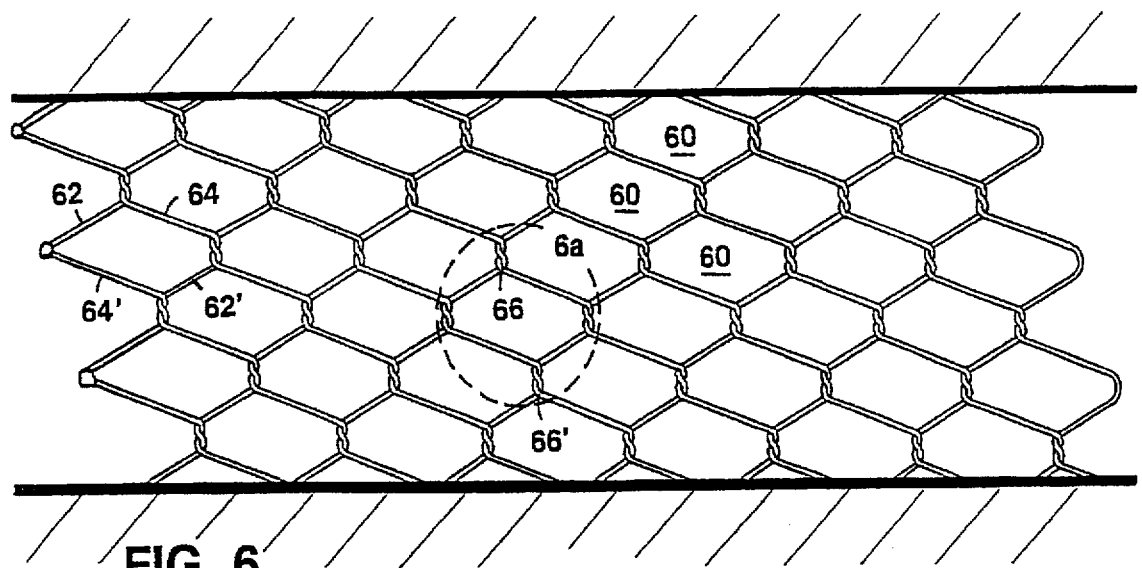
Figure 6A:
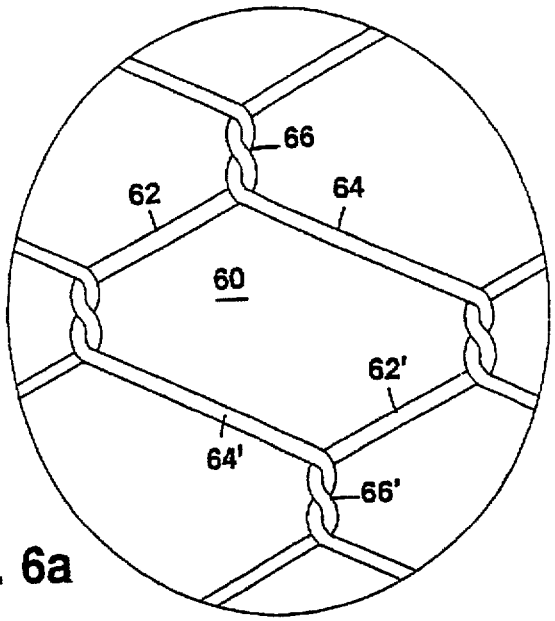
FIGS. 6a and 6b are enlarged views of the portion of the prosthesis in the region defined by line aa in FIG. 6 in an expanded and compressed state respectively.
Figure 6B:
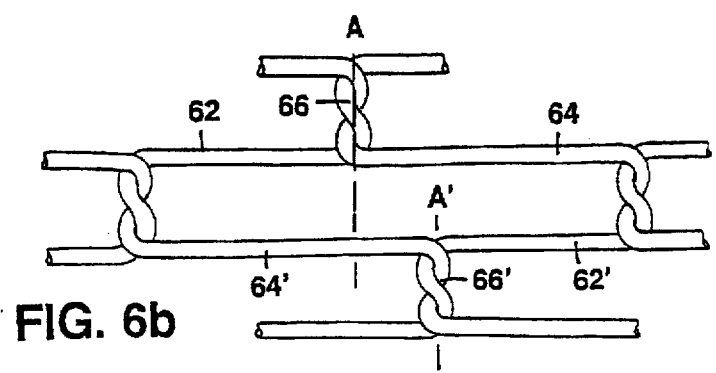

Referring to FIGS. 6–6b, the geometry of the cells can also be varied to, for example, a parallelogram configuration. Referring particularly to FIGS. 6 and 6a, the cells 60 are formed with short sides 62, 62', long sides 64, 64' and joints 66, 66'. The joints formed by helically wrapping the strands at the points of intersection, as described above, but opposing joints are offset axially. Referring to FIG. 6b, when the stent is compressed, the joints 66, 66' are disposed adjacent each other. This feature allows the prosthesis to be compressed to very small sizes since the joints on opposing sides of the cells do not interfere.

Figure 7:
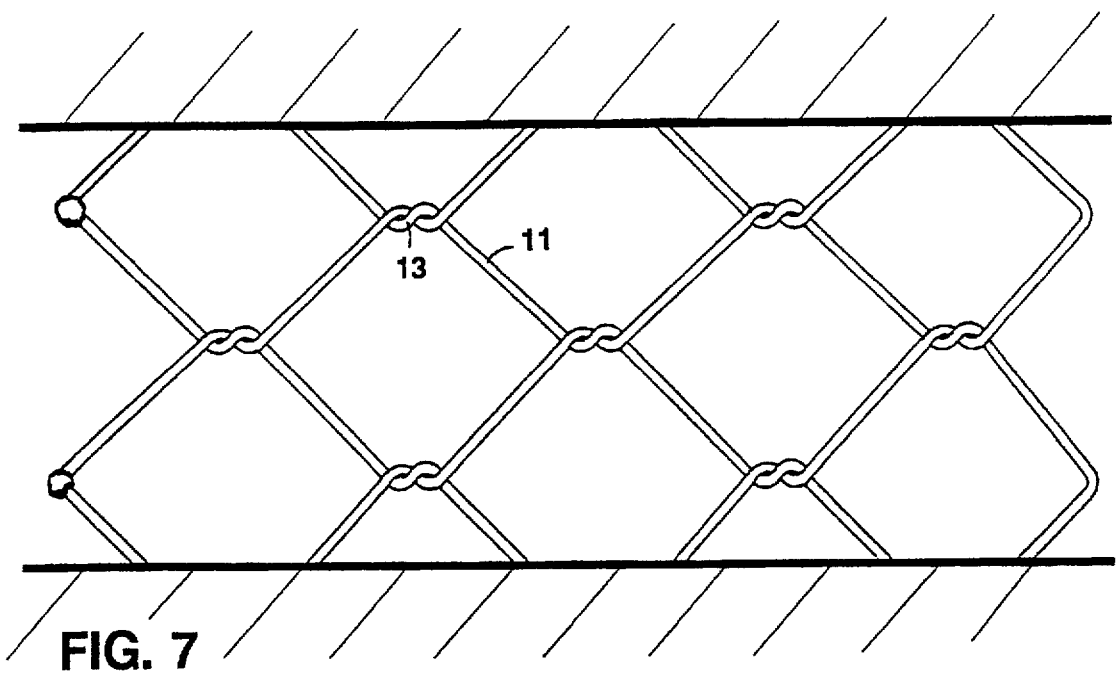
Figure 7A:
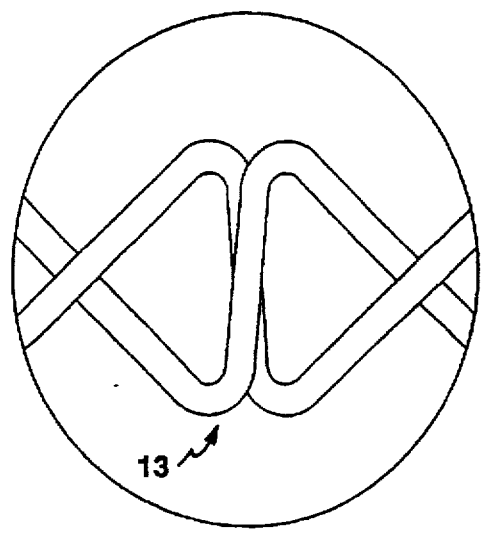
FIGS. 7a and 7b are enlarged views of a portion of the prosthesis when the prosthesis is compressed and expanded, respectively.
Figure 7B:
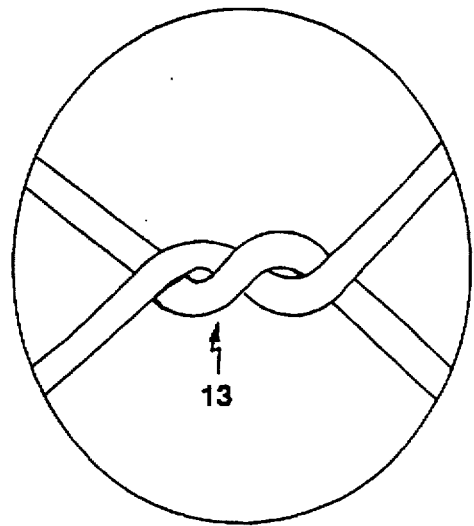

Referring to FIGS. 7–7b, in another prosthesis, the orientation of the interlocking joint 13 may be placed so that the axes of the helices are parallel to axis of the prosthesis. Referring to FIG. 7a, in this orientation, separation may occur at the interlocking joint 13 during high radial compression. The integrity of the joint can be maintained by wrapping the strands through multiple 360° rotations at the joints.

In embodiments, the prostheses according to the invention may be sized and constructed for use in various body lumens, such as, for example, blood vessels, e.g. coronary or peripheral vessels, the esophageal tract, the bronchial tract, or the urethra. The prosthesis can be used in applications, where the prosthesis experiences repeated compression and expansion (e.g., peristaltic action or lumen wall stretching, as in the vascular system) since the joint structure of the prosthesis enables relative movement within the cell structure of the prosthesis without fatigue failure. In a particular embodiment, the cell structure is used as a scaffold to carry a covering or other physiologically useful member. For example, the prosthesis may be constructed for use as an aortic graft by providing a dacron sleeve over the cell structure. The prosthesis has particular advantages in such applications, since the sleeve material can fold into the large open areas of the cells when the prosthesis is compressed which allows the prosthesis to be compressed to small diameters. The prosthesis can be constructed for drug delivery by providing a drug-incorporating membrane or coating. Such a coating, a drug-incorporated hydrogel, is described in U.S. Ser. No. 08/097,248, filed Jul. 23, 1993, the entire contents of which is incorporated herein by reference. A fabric sleeve such as, for example, dacron, may be coated or soaked with drug, prior to delivery into the body. The drug may be, for example, heparin, anti-hyperplasia drugs, or anti-tumor drugs.

Figure 8:
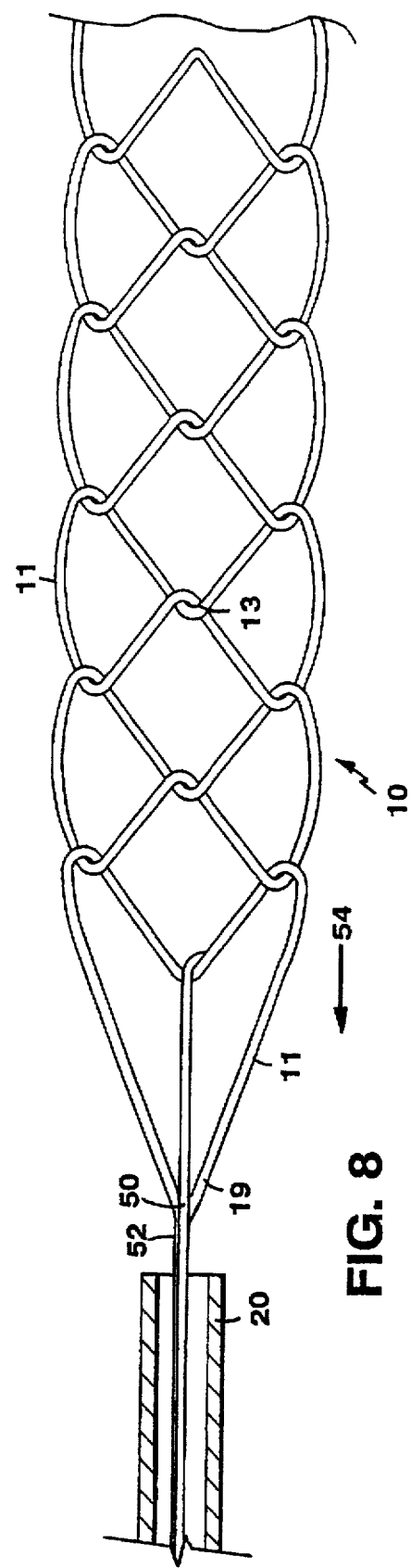
FIG. 8 is a cross-sectional side view of another medical prosthesis.

Referring to FIG. 8, in another embodiment, a prosthesis is constructed to be placed within a body lumen temporarily. In this embodiment, the strands 11 of the medical prosthesis do not terminate at a proximal open end. Instead, the strands 11 extend to a common point 50 where they are joined (e.g. by welding or tying) to a retracting wire or tube that extends further through sheath 20 to a location outside the body. This enables the medical prosthesis 10 to be pulled proximally back into the delivery system in the direction of arrow 54 after it has been deployed.

Alternatively, the proximal end 19 of the medical prosthesis 10 may be formed in the geometric cellular pattern, as discussed previously, however, the ends of the cells at the proximal end 19 may be brought together to a common point by a connector, such as, for example, a tether (not shown). The tether is attached to the delivery system. In this embodiment, the medical prosthesis may be temporarily deployed since the tether enables the device to be pulled proximally back into the delivery system. The medical prosthesis 10 may also be left in the body by removing the tether (e.g., by cutting it or untying it), enabling the proximal end of the prosthesis to be fully deployed and expanded to its tubular shape against the wall of a body lumen.

In still other embodiments, the prosthesis may be of the non-self-expanding type, preferably delivered using a catheter having an expandable balloon. These stents provide advantages in that the cell and joint structures adjust with the elastic limits of the strand material, which may be, for example, tantalum, titanium, or stainless steel. The stents also provide advantages in ease of manufacture. A particular application for such prostheses are stents for treatment of stenoses in arteries and as aortic grafts for spanning aneurysms.

In still other embodiments, the prosthesis may be formed of a temperature-sensitive shape memory material with a transition temperature around body temperature. The prosthesis can then be delivered in a compressed condition in one superelastic crystalline state and expand by crystalline phase transformation in response to exposure to body temperature.

In still further embodiments, different portions of a prosthesis may have variations in construction to vary properties at a particular location. For example, the ends of a prosthesis may be constructed to increase the number of cells around the circumference so as to provide a large radial force to firmly anchor the prosthesis in the lumen, while the mid-portions of the prosthesis have a smaller number of cells around the circumference to provide a somewhat lower radial force.

Still other embodiments are in the following claims.

What is claimed is:

1. An implantable medical prosthesis, comprising:

a tube-form body with a body wall structure having a geometric pattern of cells defined by a plurality of elongate strands extending to regions of intersection, and interlocking joints at said regions of intersection formed by a portion of at least one of said strands being helically wrapped through an angle of at least 360° about a portion of another said strand to form helically wrapped portions each having an axis, each strand in a cell having a strand angle relative to an axis of a joint in the cell that decreases upon circumferential expansion of the body, said interlocking joints constructed such that the axes of the helically wrapped portions are oriented substantially circumferentially with respect to said tube-form body.

2. The prosthesis of claim 1 wherein portions of each of said plurality of strands are helically wrapped about each other.

3. The prosthesis of claim 1 wherein said interlocking joints are constructed such that the helically wrapped portions of said strands can move relative to each other when the prosthesis is subject to varying radial compressive forces while still maintaining said cell structure.

4. The prosthesis of claim 1 wherein said interlocking joints are constructed with said strands helically wrapped through a single 360 degree rotation.

5. The prosthesis of claim 1 wherein the said prosthesis is self-expanding.

6. The prosthesis of claim 1 wherein said strands are metal wires composed of a Nickel-Titanium alloy.

7. The prosthesis of claim 1 further including a sleeve-type covering.

8. The prosthesis of claim 1 fully constructed for use in the biliary system having a fully expanded diameter of about 10 mm, and compressible to a diameter of about 9 French.

9. The prosthesis of claim 1 constructed to plastically deform during expansion.

10. The prosthesis of claim 1 constructed of a shape memory material to enable expansion in response to a temperature change.

11. The prosthesis of claim 1 including a drug-delivery layer carried by said wall structure.

12. The prosthesis of claim 1 constructed as a temporary stent, with an end of said stent connected to a drawing member that permits withdrawing of said stent after deployment.

13. The prosthesis of claim 1 wherein the tube form body has a compressed state and an expanded state such that the strand angle is in the range of 35°–55° in the expanded state.

14. The prosthesis of claim 1 wherein a strand at a helically wrapped portion has a single 360° rotation relative to a second strand at the helically wrapped portion.

15. The prosthesis of claim 13 wherein each cell has a diamond shaped geometry in the expanded state.

16. The prosthesis of claim 13 constructed as a temporary stent, with an end of said stent connected to a drawing member that permits withdrawing of said stent after deployment.

17. The prosthesis of claim 1 wherein tube-form body expands from a compressed state to an expanded such that the strand angle in the expanded state is less than the strand angle in the compressed state.

18. A system for treating an occluded body lumen, comprising;
   a prosthesis having a tube-form body with a body wall structure having a geometric pattern of cells defined by a series of elongate strands extending to regions of intersection, and interlocking joints at said regions of intersection formed by portions of said strands that are helically wrapped about each other through an angle of at least 360° to form helically wrapped portions each having an axis, said interlocking joints constructed such that the axes of the helically wrapped portions are oriented substantially circumferentially with respect to said tube-form body, and
   a delivery catheter constructed to receive said prosthesis in a compact state for delivery through the body to a desired site in said body lumen, the prosthesis having a length and a diameter in the compact state, and to allow expansion of said prosthesis to a larger diameter and a smaller length for engaging said body lumen at said desired site.

19. The system of claim 18 wherein said delivery catheter includes a sheath constructed to maintain said prosthesis in compact form during said delivery.

20. The system of claim 18 wherein said interlocking joints are constructed such that the helically wrapped portions of said strands can move relative to each other when the prosthesis is subject to varying radial compressive force while still maintaining said cell structure.

21. The system of claim 20 wherein said strands are helically wrapped through a single 360 degree rotation.

22. The system of claim 21 wherein said strands are metal wires composed of an Nickel-Titanium alloy.

23. The system of claim 22 fully constructed for use in the biliary system having a fully expanded diameter of about 10 mm, and compressible to a diameter of about 9 French.

24. A method for treating a body lumen, comprising:
   providing a prosthesis having a tube-form body with a body wall structure having a body length and a geometric pattern of cells defined by a series of elongate strands extending to regions of intersection, and interlocking joints at said regions of intersection formed by portions of said strands that are helically wrapped about each other through an angle of at least 360° to form helically wrapped portions each having an axis, said interlocking joints constructed such that the axes of the helically wrapped portions are oriented substantially circumferentially with respect to said tube-form body,
   providing a delivery catheter constructed to receive said prosthesis in a compact state for delivery to a desired site in said body lumen and to allow expansion of said prosthesis to a larger diameter for engaging said body lumen at said desired site,
   delivering said prosthesis to said site on said catheter, and
   releasing said prosthesis at said site such that the body length is reduced upon expansion of the diameter of the prosthesis.

25. The method of claim 24 comprising:
   a method of treating a body lumen having a highly tortuous bend, by providing and delivering said prosthesis to said bend.

26. The method of claim 25 wherein said bend approaches 80°–90°.

27. The method of claim 24 wherein the delivering step further comprises introducing the prosthesis into a biliary tract of a patient.

28. The method of claim 27 wherein the prosthesis is extending along a curve in the biliary tract.

29. An implantable medical prosthesis comprising:
   a tube-form body with a body wall structure having a geometric pattern of cells defined by a plurality of elongate strands extending to regions of intersection, the tube-form body having a compact state and an expanded state; and
   interlocking joints formed by a portion of at least one of said strands being helically wrapped through an angle of at least 360° about a portion of another said strand, each interlocking joint having an axis extending through the helically wrapped portion, each strand in a cell having a strand angle relative to an axis of a joint in the cell in the range of 35°–55° when the tube-form body is in the expanded state, said interlocking joints constructed such that the axes of the helically wrapped portions of the interlocking joints are oriented substantially circumferentially with respect to said tube-form body.

30. The prosthesis of claim 29 wherein the interlocking joints are constructed that the axis of said helically wrapped portions of said strands can move relative to each other when the prosthesis is subject to varying radial compressive forces while still maintaining said cell structure.

31. The prosthesis of claim 29 wherein said strands are helically wrapped through a single 360 degree rotation.

32. The prosthesis of claim 29 wherein said prosthesis is self-expanding.

33. The prosthesis of claim 29 wherein said strands are metal wires composed of a Nickel-Titanium alloy.

34. The prosthesis of claim 29 further including a sleeve-type covering.

35. The prosthesis of claim 29 fully constructed for use in the biliary system having a fully expanded diameter of about 10 mm, and compressible to a diameter of about 9 French.

36. The prosthesis of claim 29 constructed to plastically deform during expansion.

37. The prosthesis of claim 29 constructed of a shape memory material to enable expansion in response to a temperature change.

38. The prosthesis of claim 29 including a drug-delivery layer carried by said wall structure.

39. The prosthesis of claim 29 constructed as a temporary stent, with an end of said stent connected to a drawing member that permits withdrawing of said stent after deployment.

40. A method for inserting a prosthesis in the biliary tract comprising:

providing a prosthesis having a tube-form body with a body wall structure having a body length and a geometric pattern of cells defined by a series of elongate strands extending to regions of intersection, and interlocking joints at said regions of intersection formed by portions of said strands that are helically wrapped about each other through an angle of at least 360° to form helically wrapped portions are oriented substantially circumferentially with respect to said tube-form body;

providing a delivery catheter constructed to receive said prosthesis in a compact state for deliver to a desired site in said biliary tract and to allow expansion of said prosthesis to a larger diameter for engaging said biliary tract at said desired site, delivering said prosthesis at said sire such that the body length is reduced upon expansion of the diameter of the prosthesis such that the prosthesis extends along a portion of the biliary tract.

41. The method of claim 40 wherein each strand in a cell has a strand angle relative to the axis of a helically wrapped portion of a joint in the cell, the strand angle decreasing upon release in the biliary tract.

* * * * *

UNITED STATES PATENT AND TRADEMARK OFFICE
CERTIFICATE OF CORRECTION

PATENT NO.     : 5,800,519
DATED          : September 1, 1998
INVENTOR(S)    : David L. Sandock It is certified that error appears in the above-identified patent and that said Letters Patent is hereby corrected as shown below:

<u>Title page,</u>
Item [73], Assignee, delete "Kopin Corporation, Taunton, Mass." and substitute therefor -- SciMed Life Systems, Inc., Maple Grove, Minnesota --.

Signed and Sealed this

Twelfth Day of November, 2002

*Attest:*

JAMES E. ROGAN
*Attesting Officer*   *Director of the United States Patent and Trademark Office*